US010362830B2

(12) United States Patent
Campbell

(10) Patent No.: US 10,362,830 B2
(45) Date of Patent: Jul. 30, 2019

(54) PAIN REDUCING FOOTWEAR AND SYSTEMS AND METHODS FOR USING SAME

(71) Applicant: Ben R Campbell, Atlanta, GA (US)

(72) Inventor: Ben R Campbell, Atlanta, GA (US)

(*) Notice: Subject to any disclaimer, the term of this patent is extended or adjusted under 35 U.S.C. 154(b) by 0 days.

(21) Appl. No.: 15/880,407

(22) Filed: Jan. 25, 2018

(65) Prior Publication Data

US 2018/0213879 A1 Aug. 2, 2018

Related U.S. Application Data

(60) Provisional application No. 62/451,705, filed on Jan. 28, 2017.

(51) Int. Cl.
| | | |
|---|---|---|
| *A43B 3/00* | (2006.01) | |
| *A61H 23/02* | (2006.01) | |
| *A61F 5/14* | (2006.01) | |
| *A43B 7/14* | (2006.01) | |

(52) U.S. Cl.
CPC .......... *A43B 3/0005* (2013.01); *A43B 7/1415* (2013.01); *A61F 5/14* (2013.01); *A61H 23/02* (2013.01); *A61H 2201/02* (2013.01); *A61H 2201/164* (2013.01); *A61H 2201/5002* (2013.01); *A61H 2201/5097* (2013.01)

(58) Field of Classification Search
CPC .... A43B 3/0005; A43B 7/1415; A61H 23/02; A61H 2201/5002; A61H 2201/5097; A61H 2201/164; A61H 2201/02; A61H 23/00; A61H 23/0254; A61H 23/0263; A61H 23/0272; A61H 23/0281; A61H 2201/1642; A61H 2205/12; A61H 2205/125; A61F 5/14
See application file for complete search history.

(56) References Cited

U.S. PATENT DOCUMENTS

| | | | |
|---|---|---|---|
| 4,979,502 A | * | 12/1990 | Hunt ...................... A61H 23/02 601/15 |
| 5,592,759 A | | 1/1997 | Cox |
| 5,601,529 A | * | 2/1997 | Wollman ........... A61H 23/0263 601/70 |
| 6,234,987 B1 | | 5/2001 | Chen |
| 7,210,253 B2 | | 5/2007 | Yu |
| 7,462,158 B2 | | 12/2008 | Mor |
| 7,832,124 B2 | | 11/2010 | Blockton |
| 8,322,055 B1 | | 12/2012 | Saint-Cyr |
| 10,076,460 B2 | | 9/2018 | Harry |
| 10,172,762 B1 | | 1/2019 | Branch |

(Continued)

*Primary Examiner* — Quang D Thanh
(74) *Attorney, Agent, or Firm* — Bekiares Eliezer LLP

(57) ABSTRACT

A footwear and systems for reducing foot pain or discomfort. An article of footwear includes: an upper; a sole, at least one vibration device disposed within the upper, the vibration device including at least one vibrational element capable of delivering vibrations to a user of the footwear; a controller communicatively connected to the vibration device and configured to control operation of the one or more vibration devices based on instructions regarding operation of the vibration device; and a control unit communicatively connected to the controller and configured to transmit instructions regarding the operation of the vibration device to the controller. Methods for reducing pain and discomfort are provided using the footwear, devices and systems.

18 Claims, 9 Drawing Sheets

(56) References Cited

U.S. PATENT DOCUMENTS

| | | | |
|---|---|---|---|
| 2008/0262393 A1* | 10/2008 | Docherty | A61F 7/007 601/15 |
| 2009/0007458 A1 | 1/2009 | Seiler | |
| 2011/0047828 A1* | 3/2011 | Shuster | A43B 3/0005 36/112 |
| 2012/0023785 A1 | 2/2012 | Barnes | |
| 2012/0046579 A1* | 2/2012 | Radl | A61H 11/00 601/46 |
| 2012/0186101 A1* | 7/2012 | Sanchez | A43B 3/0005 36/44 |
| 2012/0222333 A1* | 9/2012 | Short | A43B 3/0005 36/140 |
| 2013/0204169 A1* | 8/2013 | Poepperling | A61H 9/0078 601/46 |
| 2013/0203952 A1 | 11/2013 | Fujiyama et al. | |
| 2018/0036531 A1 | 2/2018 | Schwarz et al. | |
| 2018/0338561 A1 | 11/2018 | Destrian et al. | |

\* cited by examiner

PAIN REDUCING FOOTWEAR AND SYSTEMS AND METHODS FOR USING SAME

CROSS REFERENCE TO RELATED APPLICATIONS

This application claims the benefit of priority to U.S. Provisional Patent Application Ser. No. 62/451,705, filed Jan. 28, 2017, which is hereby incorporated herein by reference in its entirety.

FIELD OF INVENTION

The present invention relates to methods, footwear and systems for reducing pain.

BACKGROUND OF THE INVENTION

The negative effects of foot pain and discomfort can greatly affect people quality of life, and even have negative systemic effects. The discomfort one may experience from the pain in their feet will normally lead to stress and other discomfort in the human body. For example, individuals experiencing arthritis may often experience mental stress in addition to the foot pain associated with the arthritis. Current treatment options are limited, and often involve pharmaceuticals, which can substantial side effects.

Accordingly, there remains a need for new footwear and treatment methods which are capable of reducing pain without the use of pharmaceuticals. This need and other needs are satisfied by the various aspects of the present disclosure.

SUMMARY OF THE INVENTION

In accordance with the purposes of the invention, as embodied and broadly described herein, the invention, in one aspect, relates to footwear and systems for reducing pain, such as muscle or nerve pain in the foot.

In another aspect, the invention relates to an article of footwear that includes at least one vibration device, which may be controlled by a user using a control unit, such as, for example, a wireless device or mobile device or in another manner. When a user activates the vibration device in the article of footwear, the vibration device may be configured to transmit vibration effects. If the user is wearing the article of footwear, the vibration device may vibrate against the user's foot upon activation. In further aspects, the vibration device may not be located on the sole of the foot and may have no direct physical contact with the sole of the foot.

In another aspect, the invention may allow the user to adjust the vibration of one or more of the vibration device(s) in the article of footwear by using a wireless device running application software (an "app"). For example, the user may use the wireless device to vibrate one or more of the vibration device(s) in the article of footwear at a low or first level, a medium or second level, or a high or third level. Other embodiments may allow for only two levels of vibration, more levels of vibration, and/or a continuous scale of available vibration rather than discrete level(s).

In another exemplary aspect, the invention relates to a method for reducing pain in a user; the method comprising: providing an article of footwear having at least one vibration device; operatively positioning the article of footwear on the user's foot such that the at least one vibration device can provide vibration to at least one site in the user's foot; activating the at least one vibration device; and maintaining the at least one vibration device at the site of the foot for a time sufficient to reduce pain.

In further aspects, the invention also relates to methods for using the disclosed footwear and systems.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principles of the invention.

DETAILED DESCRIPTION OF THE INVENTION

Figure 1:
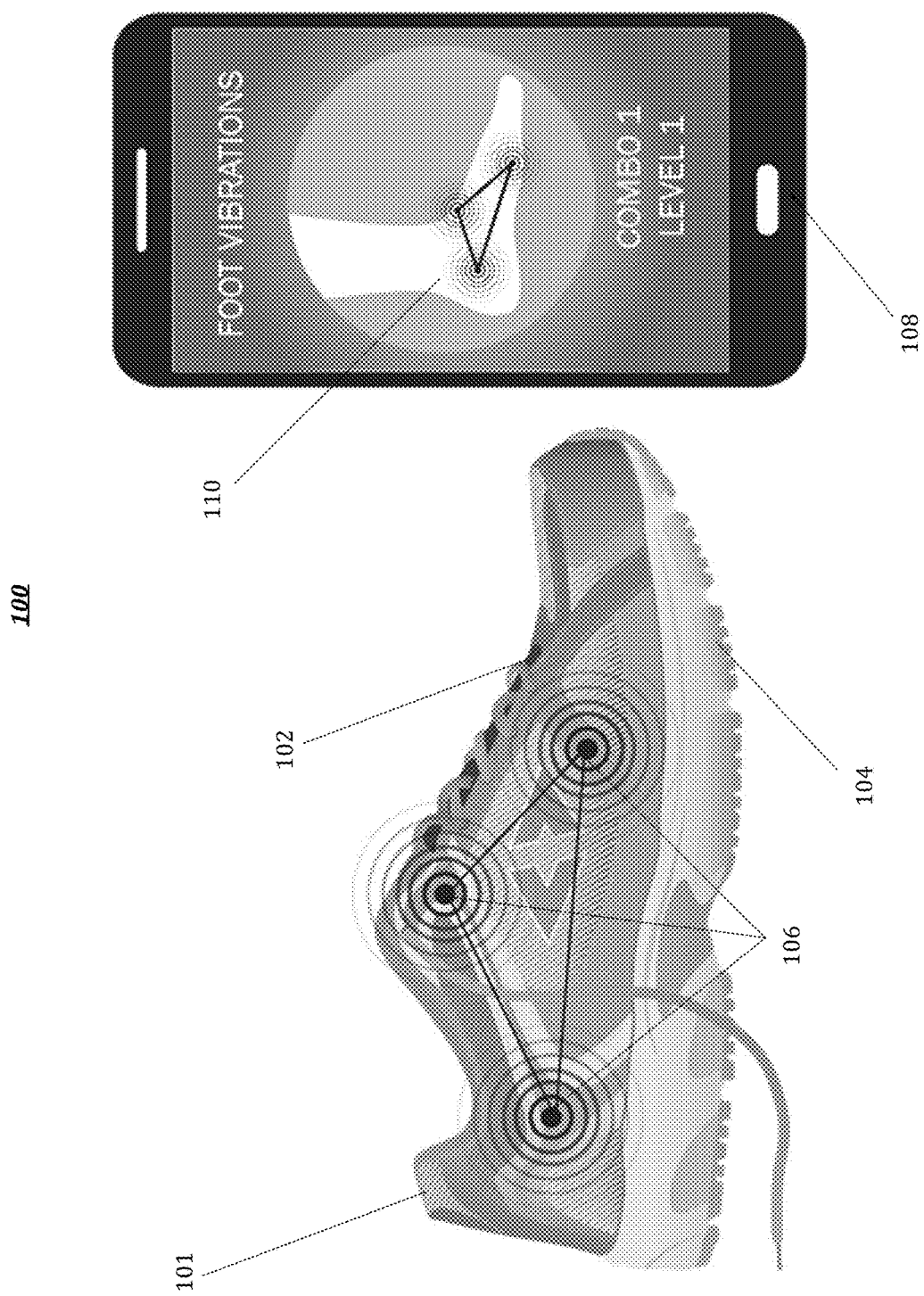
FIG. 1 shows a depiction of a footwear system in accordance with an exemplary embodiment of the present invention.

The present invention can be understood more readily by reference to the following detailed description of the invention and the Examples included therein.

Before the present articles, systems, devices, and/or methods are disclosed and described, it is to be understood that they are not limited to specific manufacturing methods unless otherwise specified, or to particular materials unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

All publications mentioned herein are incorporated herein by reference to disclose and describe the methods and/or materials in connection with which the publications are cited.

A. Definitions

It is also to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "an assembly" includes two or more assemblies.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

The terms "first," "second," "first part," "second part," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally affixed to the surface" means that it can or cannot be fixed to a surface.

As used herein, the term "footwear" means any item that may be worn on a foot. For example, an article of footwear may be, but is not limited to, a shoe, a slipper, a boot, a ski boot, a snowboard boot, a scuff, a clog, a sandal, a moccasin, a loafer, or anything of the like. As another example, an article of footwear may be, but not limited to, a sock, a stocking, a legging, a foot wrap, or the like. As used herein, the phrase "article of footwear" shall include any item that may include one or more vibrating device(s) whose vibration may be controlled by a user using his or her wireless device, and the phrase "article of footwear" shall include, but not be limited to, at least all of the types listed in this paragraph. As noted, the invention is described herein with regard to an "article of footwear." Generally, a user wears a pair rather than just one article of footwear. The invention may include an embodiment where both of the pair or only one of the pair may include the vibration device(s).

Disclosed are the components to be used to manufacture the disclosed devices and articles of the invention as well as the materials themselves to be used within the methods disclosed herein. These and other materials are disclosed herein, and it is understood that when combinations, subsets, interactions, groups, etc. of these materials are disclosed that while specific reference of each various individual and collective combinations and permutation of these materials cannot be explicitly disclosed, each is specifically contemplated and described herein. For example, if a particular material is disclosed and discussed and a number of modifications that can be made to the materials are discussed, specifically contemplated is each and every combination and permutation of the material and the modifications that are possible unless specifically indicated to the contrary. Thus, if a class of materials A, B, and C are disclosed as well as a class of materials D, E, and F and an example of a combination material, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the articles and devices of the invention. Thus, if there are a variety of additional steps that can be performed it is understood that each of these additional steps can be performed with any specific aspect or combination of aspects of the methods of the invention.

It is understood that the devices and systems disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Pain Reducing Footwear and Systems

As briefly described above, the present disclosure relates, in various aspects, to footwear and systems for reducing pain or discomfort, such as arthritis, muscle pain or nerve pain in the foot, or the like. In further aspects, the disclosed footwear and systems for reducing pain or discomfort can be used to treat any type of foot pain. In still further aspects, the disclosed footwear and systems can also be used to reduce pain and stress throughout the body, for example by stimulating the central nervous system. In some aspects, the disclosed footwear and systems may be used by individuals who are not experiencing any pain in their feet, but to relax the nerves in the feet and to help reduce nerve tension and mental stress in the entire body. In other aspects, the disclosed footwear and systems may be used to relieve any type of stress in the body or mind.

In one aspect, the present disclosure provides an article of footwear comprising: an upper; a sole; at least one vibration device disposed within at least one of: the upper and sole, the vibration device comprising at least one vibrational element capable of delivering vibrations to a user of the footwear; a controller communicatively connected to the vibration device and configured to control operation of the one or more vibration devices based on instructions regarding operation of the vibration device; and a control unit communicatively connected to the controller and configured to transmit instructions regarding the operation of the vibration device to the controller.

In another aspect, the present disclosure provides a system for reducing foot pain, the system comprising an article of footwear; at least one vibration device disposed within a portion of the footwear, the vibration device comprising at least one vibrational element capable of delivering vibrations to a user of the footwear; a controller communicatively connected to the vibration device and configured to control operation of the one or more vibration devices based on instructions regarding operation of the vibration device; and a wireless unit communicatively connected to the controller and configured to transmit instructions regarding the operation of the vibration device to the controller.

According to various aspects of the invention, the footwear and systems of the present disclosure can comprise multiple configurations. FIG. 1 shows an exemplary embodiment of a system 100 for reducing foot pain in accordance with the present invention. As shown, the system 100 comprises an article of footwear 101 comprising an upper 102; a sole 104; and three vibration devices 106 disposed within the upper; and a control unit 108 in the form of a mobile device. This mobile device and footwear are equipped with wireless technology to allow communication with an app on the mobile device. As shown in FIG. 1, the app provides graphical user interface 110 showing a graphical image of the user's foot to indicate location and characteristics of the vibrations being delivered by the vibration devices 106 at the time of operation.

Consistent with embodiments of the present disclosure, the invention is described as including one or more vibration devices. If the invention is used in a pair of articles of footwear, generally, each of the articles will have the same number of vibration devices, but not necessarily so. In further aspects, some embodiments of the invention, however, may provide only one of the pair of articles of footwear with one or more vibration devices, while the other of the pair does not have any vibration devices. In still further aspects, other embodiments of the invention, in contrast, may provide one of the articles of a pair with more vibration devices than the other. In yet further aspects, the one or more vibration devices in each of a pair of articles of footwear need not be identical between the articles of footwear in the pair. For example, a user may have a pair of articles of footwear according to an embodiment of the invention wherein one of the articles has stronger or more robust vibration devices than the other, differently sized vibration devices than the other, differently positioned vibration devices than the other, etc.

In further aspects, the invention includes one or more vibration device in each article of footwear. In still further aspects, each article of footwear may comprise a plurality of vibration devices. In yet further aspects, the vibration device is configured to produce vibration upon activation. If the user is wearing the article of footwear on his or her foot, the vibration device vibrates at least between the user's foot and the article of footwear. In an embodiment of the invention, the vibration device may vibrate directly against the foot of the wearer of the article of footwear.

In various aspects, vibration device may further comprise a casing configured to house one or more components. In further aspects, the casing may be shaped to conform to the contour of a surface of the foot, may be configured to contains at least one vibratory element, and an optionally a thermal element. In some aspects, a casing or at least one surface of a casing, may be substantially planar to fit a flat surface of the foot. In other aspects, a casing or at least one surface of a casing, may be shaped to fit a curved surface of the foot. For example, one surface of a casing may be concave, shaped like the inner surface of a circle, and when the device contacts a surface, such as the top portion of a foot, the concave surface of the casing substantially contacts the foot surface, meaning that a majority of the concave surface is in contact with the area of the surface. This contact of substantially the entire concave surface of the device allows for enhanced transfer of vibration and/or thermal effect to the surface.

The casing may be manufactured of a flexible or pliant material such as for illustrative purposes a natural or synthetic woven or non-woven fabric, a rubber or other flexible polymer material, a silicone-based material, or may be a rigid material, such as a plastic, metal or wooden casing, wherein the casing is a container with walls to define an enclosed area. Other flexible or pliant or other materials may be employed. A material that will transfer vibrations is contemplated by the present invention.

The casing can be any shape, and may be in the shape of a three-dimensional polygon and the casing walls may define an interior space or interior sections for containing the operating elements of the invention. Any other shape (as used herein, the term shape is used in the broad sense of three-dimensional works) may be employed, so long as the shape is large enough and structured so as to be able to contain the various working components of the invention as more fully disclosed below.

In further aspects, the casing may comprise an application area configured to transmit vibration to the user's foot. In still further aspects, application area may comprise the portion of the casing for contacting the surface of the foot or for contacting a thermal element that in turn contacts the surface of the foot. In still further aspects, the application area may be all or a portion of the proximal side of a vibratory device. A thermal element cooperates with the application area to apply cold or heat to the subject, and a vibrational source cooperates with the application area to apply vibration to the subject. The placement of the thermal element is variable so long as the effects of the thermal element can be felt on the subject so as to produce thermal vasodilation or vasoconstriction. The placement of the vibrational source in the casing is variable so long as the vibrational effects of the vibrational source can be felt on the subject so as to produce vibrational vasodilation or is effective in stimulating nerves so that a pain or sensation message is blocked or interfered, and interfering with the perception of the pain or sensation by the user. The walls of the casing define an interior space that, is sized to contain at least one vibrational element, wiring to connect at least the vibrational source and a power source, and optionally a thermal element.

Figure 2:
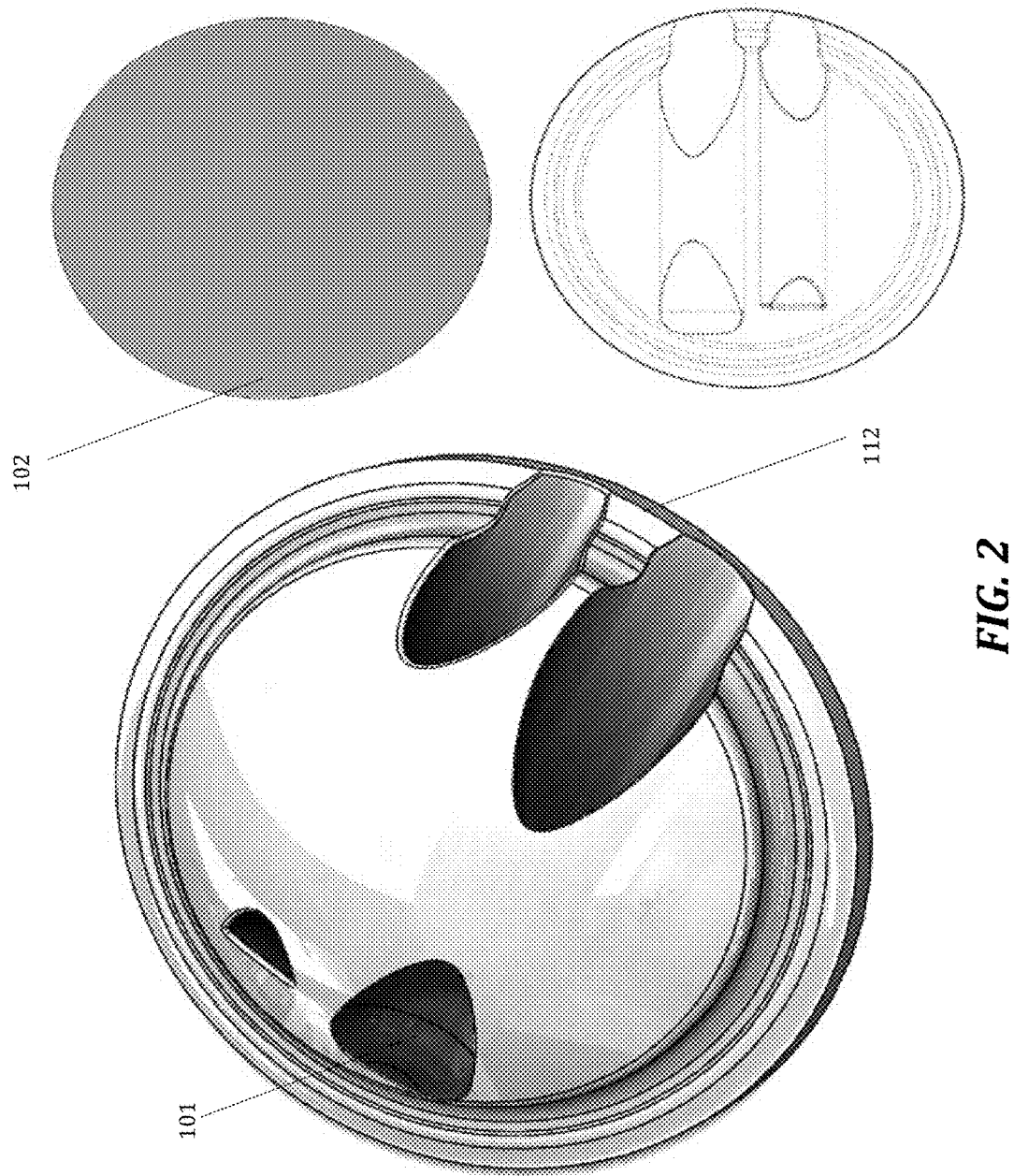
FIG. 2 shows various views depicting of a vibration device casing in accordance with an exemplary embodiment of the present invention.

FIG. 2 shows exemplary embodiment of a vibration device casing in accordance with the present invention. As shown, the vibration device casing 112 includes two cylindrical interior sections sized and shaped to contain two vibrational elements. In further aspects, the walls of the interior sections 113 define the interior space, and in some embodiments, have a low percentage of open space once the vibrational elements are positioned in the casing. In still further aspects, the vibration device casing is substantially free of open space between the interior casing walls and the vibrational elements. Without wishing to be bound by a particular theory, the absence of open space can allow for substantially all of the vibrational energy emitted from the vibrational elements to be transmitted through the casing to the user's foot. As shown, a proximal surface 115 of the casing, may be substantially planar to fit a flat surface of the foot. In other embodiments, the proximal surface of the casing may be concave, shaped like the inner surface of a circle, and when the device contacts a surface, such as the top portion of a foot, the concave surface of the casing substantially contacts the foot surface, meaning that a majority of the concave surface is in contact with the area of the surface.

Figure 3:
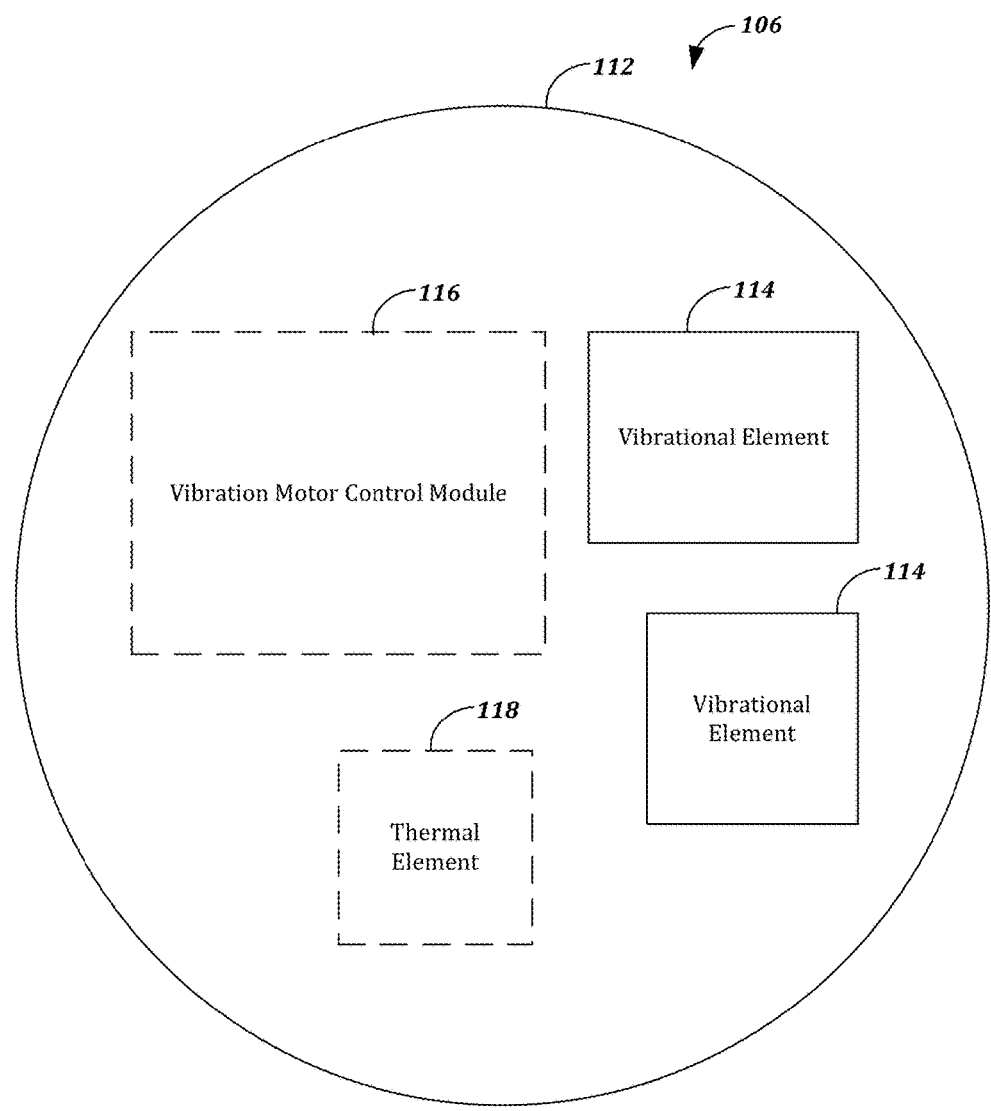
FIG. 3 shows a diagram depicting a vibration device in accordance with exemplary embodiments of the present invention.

FIG. 3 shows a diagram of exemplary embodiments of a vibration device in accordance with the present invention. As shown, the vibration device 106 comprises a pair of vibrational elements 114 contained within the vibration device casing 112. In some embodiments, the vibration device may further optionally contain a thermal element and/or a vibrational motor control module 116 as shown in dashed lines. In other embodiments, the vibrational motor control module 116 may be located remotely or outside of the vibration device casing 112.

In further aspects, vibration effects can be provided by any desired vibrational element such as, for illustrative purposes, a vibratory motor provided within the casing. Once vibration is activated by providing power to the vibratory element, such as a vibratory motor, the vibration may be constant and continual, or the vibration may be intermittent, and cycle on and off at the same or a different vibration speed or frequency. Though not wishing to be bound by any particular theory, it is believed that intermittent vibration may aid in reducing or preventing habituation by the body to the vibrations. In further aspects, the vibration device may comprise one or more vibration elements. In still further aspects, the vibration device may comprise a plurality of vibration elements. In yet further aspects, the size of the area of the user's foot against which the vibration vibrates may depend upon the size of the vibration element of the vibration device. For example, a larger vibration element in a vibration device may vibrate against a larger area of a user's foot than a smaller vibration element in a vibration device according to this embodiment.

In further aspects, the vibration elements can be any conventional vibrational source or means for producing vibrations. Non-limiting examples of suitable vibration elements include elliptical flywheel motors, eccentric motors, and the like. It is only important that the vibration element be able to transfer vibration to the subject at a sufficient level to produce the effect intended in the disclosed methods. For example, and without limitation, vibration elements in a vibration device of the present invention can provide vibrations of between about 75-500 Hz. In some aspects, the application area of the device which vibrates due to the action of the vibrational source may applied to one or more areas of the user's foot for a time period sufficient to accomplish the effect intended in the disclosed methods, which can be between 1 second to several minutes or more depending on the user, conditions and/or the method. For example, the application area of the casing may provide vibration to the subject for a period of about 1 second to about 120 seconds, or longer in certain methods, to accomplish the effect intended in the disclosed methods. In some aspects, a vibration element may be a high frequency low amplitude eccentric motor. The motor may be controlled by a motor drive or motor control module, or the like.

In various aspects, the vibration level or intensity of a vibration device may be defined by reference to the amplitude and the frequency of the vibrations of the vibration device or element. To this end, the amplitude of a vibration of a vibration device is characterized as the strength or power of the vibration that the user feels when in contact with the vibration. In further aspects, high amplitude vibrations may be strong vibrations that a user feels are more powerful or forceful against his or her foot than a weak vibration having a low amplitude. In still further aspects, wherever on the spectrum of amplitude a vibration falls, the vibration also may be characterized by its frequency. In yet further aspects, a low frequency translates in this description as a slow vibration. High frequency is a quick or fast vibration. Thus, as further described herein, a vibration that may be applied by a vibration device according to the present invention may be, in various embodiments, strong and slow, weak and quick, strong and quick, weak and slow, and the ranges between.

In further aspects, embodiments of the invention may provide that all vibrations issued or transmitted by the one or more vibration devices of an article of footwear have the same frequency, but vary in amplitude. In other words, in this aspect, a vibration repeats at the same rate of time, but its strength varies. In other aspects, the opposite may be true in other embodiments of the invention where all vibrations have the same strength (amplitude), but the frequency varies. The level of vibrations in embodiments referenced in this paragraph then, according to some aspects, may be sorted into distinct levels such as low, medium, and high, and/or even to allow for a selection of a level along a continuum between low and high.

Nonetheless, embodiments that allow for variances in both frequency and amplitude of vibration of one or more vibration devices in an article of footwear may provide distinct levels of vibration for a user to choose from where each of the levels corresponds to a particular setting of frequency and amplitude. In further aspects, other embodiments may offer a user a continuum of levels from low to high even as the frequency and/or the amplitude of the vibration changes across the continuum. While the previous paragraphs of this description describe vibrations having different characteristics of frequency and amplitude, various embodiments of the invention may provide only a single level of vibration for the vibration devices of an article of footwear. In further aspects, whether an article of footwear includes one or more vibration devices, each of them may only vibrate at a single level in some embodiments of the invention.

According to further embodiments, the invention may provide for more than one level of vibration for the vibration devices of an article of footwear. For example, an article of footwear according to an embodiment of the invention may include one or more vibration devices with one or more of these devices having more than one level of vibration. Advantageously, in embodiments of the invention that include one or more vibration devices having more than one vibration level, the user of the embodiment may select the level of vibration for the vibration devices in the article of footwear. As further described herein, the vibration level selection functionality available to a user may vary from embodiment to embodiment. For example, in further aspects, a user may be able to select a level of vibration, but the same level is selected for all of the vibration devices whether the article of footwear includes one or more vibration devices. In this aspect, all the vibration devices of that particular embodiment vibrate at the same level. As another example, in other embodiments, a user may be able to select varying or different respective levels of vibration in an article of footwear having more than one vibration devices.

In some embodiments, the vibration device may be positioned with respect to the article of footwear anywhere other than the sole or bottom of the foot of the user. In other embodiments, the vibration device may be positioned anywhere on the article of footwear. In yet other embodiments, the vibration device(s) may be positioned only on the sole or bottom of the article of footwear.

Advantageously, the invention may include embodiments having different features with respect to the placement of the vibration devices in the article of footwear. In some embodiments, a user may be able to choose where to position the vibration device with respect to his or her foot and the article of footwear. In other embodiments, a user may have limited choice in where to position the vibration device. In further aspects, the vibration device may be fixed or integrated with respect to the article of footwear so the user may have little, if any, choice in positioning of the vibration device.

Wherever placed in an article of footwear, the position and/or configuration of a vibration device optimally does not interfere with the user's wearing and/or enjoyment of the article of footwear. To avoid this interference, a vibration device may be incorporated on the top of the inside of the article of footwear, or may be included within a lining of the inside of the article of footwear. In some cases, the positioning of the one or more vibration devices in an article of footwear may be sufficient to alleviate pain and/or discomfort suffered by the user without activation of the vibration device of the article of footwear.

The vibration device of the embodiments of the invention may be of any technology that achieves the function of vibrating between the foot of the user (and in an embodiment directly against the foot of a user) and the article of footwear.

The invention, as noted, includes one or more vibration devices associated with an article of footwear where the vibration devices vibrate between the user's foot and the article of footwear (and may vibrate directly against the user's foot). Vibration, as used herein, is distinguished from massage. Vibration is defined herein to be similar to a piston-like back and forth motion. In contrast, massage is understood herein to include more circular action or curve-like motion than piston-like motion of the vibrations used in the embodiments of the invention.

Even though a distinction is made herein between vibration and massage, in some embodiments of the invention, the vibration device may also deliver massage as part of the article of footwear. Other embodiments of the invention may provide for the vibration device to switch between vibration and massage. The switch may be selected by the user using the control unit or wireless device.

In some embodiments, the invention may provide an app on a wireless device configured to communicate with each of the vibration devices of the article of footwear. In further aspects, each of the vibration devices may require the appropriate elements to receive, act on the communications from the wireless device, and/or respond to the app with information.

As described in further detail herein, in other embodiments, the article of footwear may include a controller to receive the communications from the wireless device, to pass them on as instructions to the vibration device, to receive information from the vibration devices, and/or to send the information to the app on the wireless device. The controller may include elements to carry out its function. For example, the controller may include a receiver/transmitter, transceiver, and/or antenna for communicating with the wireless device. The controller may include "smart" technology such as a microprocessor, etc. to process and execute the instructions, information, and/or signal received from the control unit or wireless unit or the information received from the vibration device. As another example, the controller may be connected respectively by one or more wires (and/or other transmitters or carriers) to the one or more vibration devices of an article of footwear to transmit instructions/information to the vibration device and/or to receive information from them.

In various aspects, the controller and/or vibration device(s) of an article of footwear may require a power source depending on the configuration and construction. An exemplary power source may be a battery such as a rechargeable battery. Other power source(s) are possible. Any suitable power source may be used.

In various aspects, the controller and/or device components may be included in or integrated within various portion of the article of footwear. In further aspects, the controller and/or device components may be disposed in the collar of the article of footwear (such as in the rear collar behind the ankle of the user's foot, if the shoe design allows for such placement). In still further aspects, the controller and/or device components may be disposed in the tongue of the article of footwear. In yet further aspects, the controller and/or device components may be disposed within the sole. In even further aspects, the controller and/or device components may be disposed within the upper of the article of footwear. Other locations are possible, and may depend on the style of the article of footwear, size and/or other characteristics of the controller, etc. For example, heavier batteries may be best suited to be integrated with the sole or a lower portion of the footwear for balance and proximity to a wireless charging source in certain embodiments.

In further aspects, the vibration devices and/or footwear components can be connected to an outer surface of the upper. In still further aspects, the vibration devices and/or footwear components can be connected to an inner surface of the upper. In yet further aspects, the vibration devices and/or footwear components can be integrally connected between an outer surface and inner surface of the upper. In even further aspects, the vibration devices and/or footwear components can be connected to an outer surface of the sole. In still further aspects, the vibration devices and/or footwear components can be connected to an inner surface of the sole. In yet further aspects, the vibration devices and/or footwear components can be integrally connected between an outer surface and inner surface of the sole.

In various aspects, the vibration device arrangement and construction of the footwear can be configured to correspond to areas of a user's foot where sensory and pain transmission are greatest.

Figure 4A:
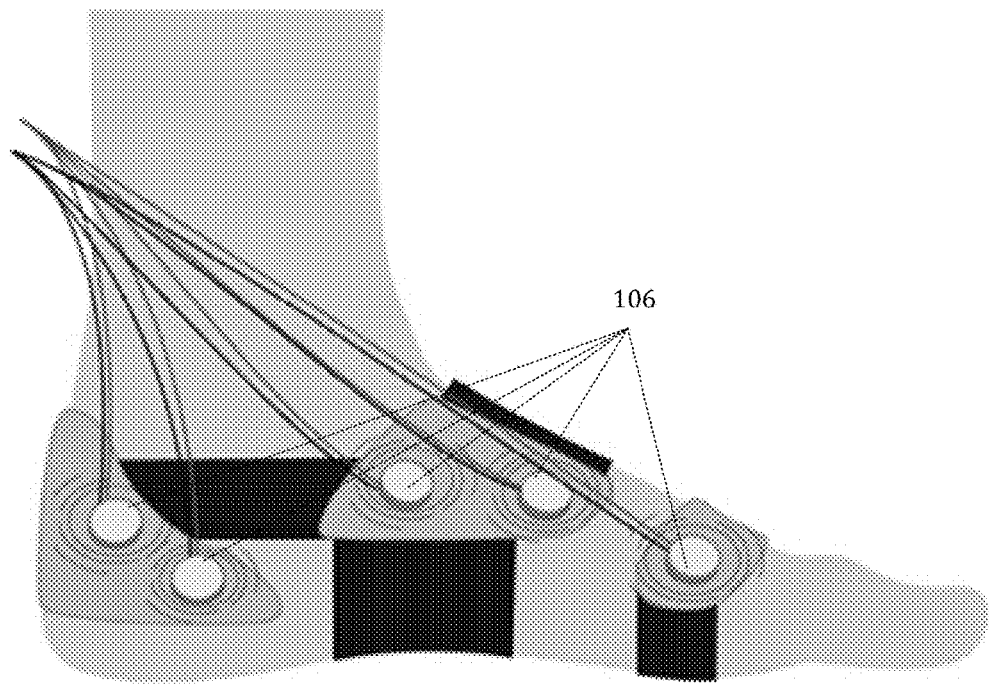
FIGS. 4A and 4B show depictions of locations where vibration devices can be applied to a user's foot in accordance with exemplary embodiments of the present invention.
Figure 4B:
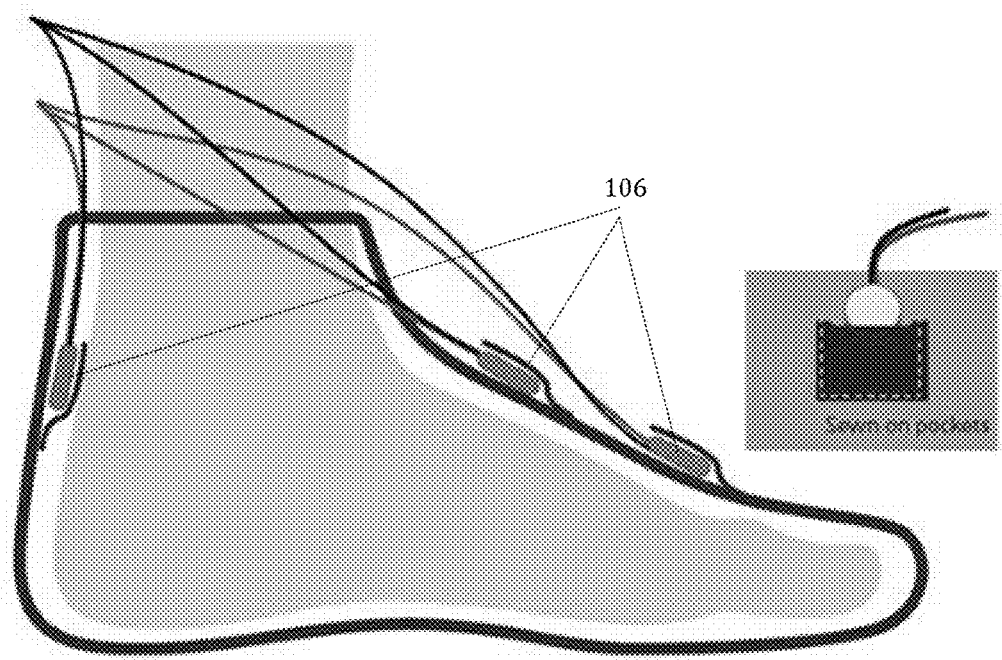

In further aspects, the vibration devices can be connected to or otherwise disposed within portions of the upper corresponding to the front of the foot, top of the foot, side(s) of the foot, and/or or heel of the foot. By way of non-limiting example, FIGS. 4A and 4B show approximate locations of the foot where one or more vibration devices can be correspondingly inserted or attached to the article of footwear.

In even further aspects, footwear may comprise a plurality of vibration devices. The plurality of vibration devices may comprise at least two vibration devices, for example, two, three, four, five, or six vibration devices, or more. In even further aspects, at least one vibration device can be connected at a location corresponding to an upper portion of the upper. In still further aspects, at least one vibration device can be connected at an upper portion of the upper adjacent to a location corresponding to the ball of a user's foot. In some aspects, the at least two vibration devices can be connected on opposite sides of the upper.

In further aspects, at least one vibration device can be connected to a rear portion of the upper. In still further aspects, at least one vibration devices at a rear portion of the upper adjacent to a location corresponding to a heel of a wearer's foot. In other aspects, a plurality of shock-absorbing members can be connected to the support frame at an upper portion of the upper adjacent to the heel of the wearer's foot.

In various aspects, the position of the vibration devices can be configured or changed with respect to the upper and sole to permit changes to the pain-relieving characteristics of the article of footwear or other foot-receiving devices. For example, positions of the vibration devices can include at least one: one on each side near or behind the ball of the feet; one on each side at the ankle position; and one or more on the top of the foot, such as, positions that primarily are associated with sensory or pain transmission.

In various aspects, the footwear can comprise an impact-dampening component or material. In further aspects, the footwear can utilize the mechanical properties and benefits of the impact-dampening component (compression spring, wave spring or the like) for shock absorption. In still further aspects, the impact-dampening component can comprise other shock absorbing materials, such as, for example, gels, air, gas, hydraulic, foam, a combination thereof or the like.

In further aspects, the device component characteristics and configuration, such as, for example, size and dimensions, can be configured to adjust for an individual user's weight, feet size, and other factors to achieve optimal load balancing and distribution. In further aspects, features of the vibration device and components may be configured or utilized to set and/or control the vibrational characteristics. For example, at least one of the following may be configured: the type of material used for the vibration device casing or housing; the vibrational element member dimensions (e.g., height, width, thickness, surface-contacting area, etc.); the flexibility or "stretchiness" of the vibration device casing material; the vibration transmission characteristics of the casing material; the percentage of open space (if any) in any portion; and the extent of exterior surface coverage of surface-contacting portion of the vibration device. In some aspects, the vibration device casing is substantially free of open space between the casing and the vibrational elements. Without wishing to be bound by a particular theory, the absence of open space can allow for substantially all of the vibrational energy emitted from the vibrational elements to be transmitted through the casing to the user's foot.

In further aspects, while the vibration devices described herein can be permanently mounted in or on an article of footwear or foot-receiving device structure, this is not a requirement. For example, the vibration devices can be connected to or disposed within a footwear insert configured to be removably mounted in footwear (or connected to a footwear assembly configured to be removably mounted on footwear or other foot-receiving device structure), e.g., to allow interchange and/or replacement of the vibration devices. Thus, according to further aspects, the present disclosure also provides a pain-reducing removable insert for an article of footwear.

In further aspects, one or more vibration devices and/or vibrational elements can be detachably connected to the upper and/or footwear, e.g., to allow interchange and/or replacement of one or more vibration elements (individually or as a unit with vibration device casing). Such configurations allow users, purchasers, retailers, or others to select desired vibrational effects and pain-reducing properties or levels in a footwear structure, e.g., for customization purposes, for personal preferences, to match desired treatment use, a user's physical characteristics, a user's symptoms, or to repair or replace defective or damaged vibration devices, etc.

In further aspects, the footwear may further comprise on opening through a wall or outer surface of the upper for providing an amplifier that is connected to the controller or a sound element contained within the footwear. In still further aspects, the footwear may comprise an opening through the outer surface for providing a light, such as an LED light, that is connected to the controller or a timing element contained within the footwear. A light (and/or sound) may be turned on when vibration is initiated and turned off when power to the vibration element is turned off. Alternatively, powering on the vibration device may also power on a timing element, and optionally a light (and/or sound), so that when a desired time period has occurred, the timing element may turn off the light (and/or sound), or may turn off a light (and/or sound) and the vibration element, or the timing element or controller may turn on sound or light after a period of vibration. Alternatively, the timing element may be under a control that is separate from a control for the vibration element. Components for switches, controller, such as a polycarbonate circuit board and the programming to accomplish the disclosed activities and others, and elements such as timing elements, sound elements and lights, are known, and can be selected or commercially acquired by those of skill in the art. Wires for connecting the elements within the footwear or on the surface are contemplated by the present invention.

In further aspects, the disclosed footwear and system may further comprise one or more of the following components: a voltage regulator, power switch (e.g., MOSFET), power management module, battery management module (e.g., fuel gauge), battery charging module, wireless power coil or receiver, wireless power control module, antenna (e.g., Bluetooth LE antenna), transceiver (e.g., Bluetooth LE transceiver), motor controller, interface module, control module, voltage sensor, current sensor, pulse-width modulation (PWM) module, power input, magnetic switch, motor control module (e.g., vibrational motor control module), and motor drive.

A number of internal components may be mounted within an interior portion of the device and/or footwear. In some aspects, the internal components may be configured in a distributed motor control configuration. In other aspects, the internal components may be configured in a centralized motor control configuration.

Figure 5:
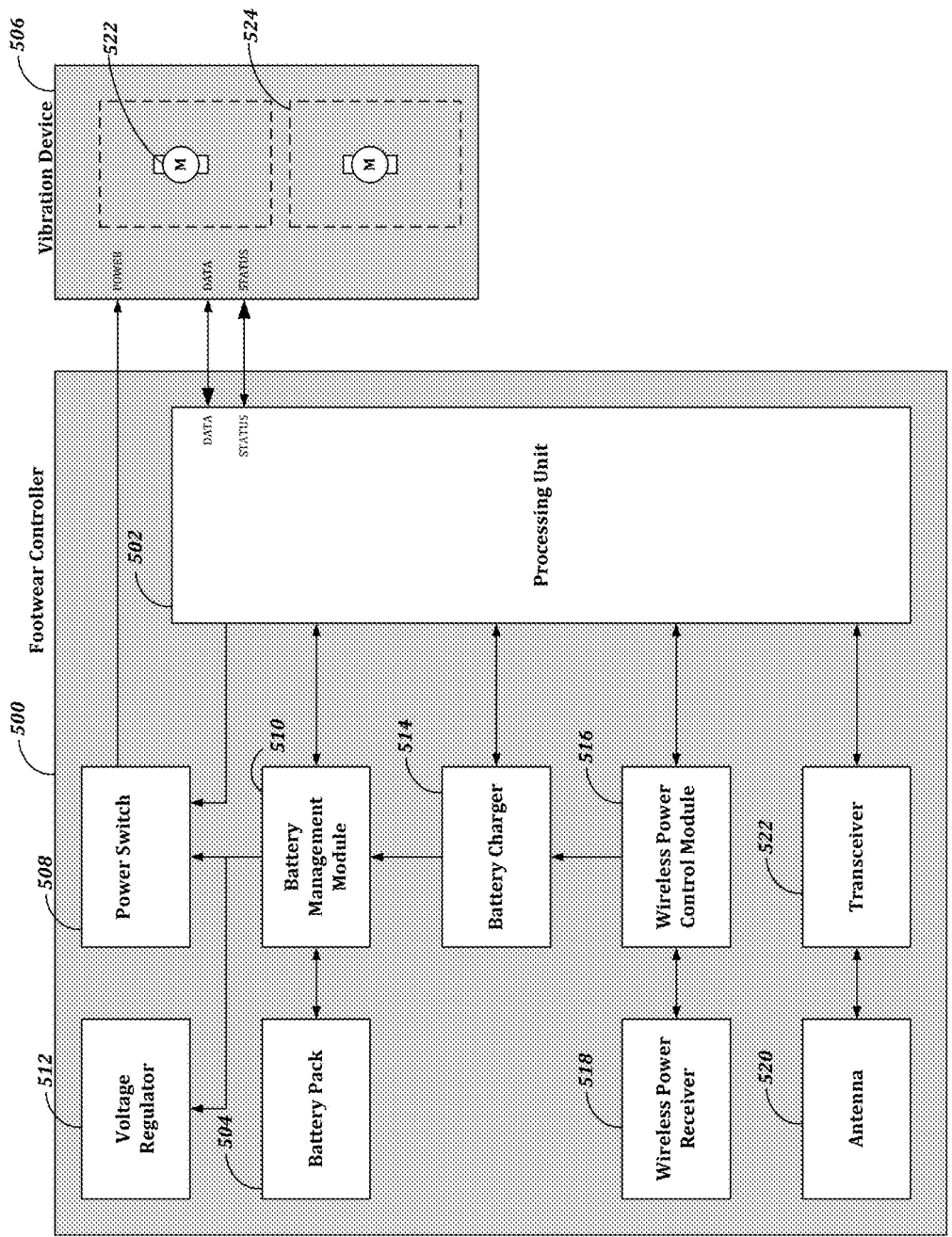
FIG. 5 show a diagram of a component configuration of the disclosed footwear in accordance with another exemplary embodiment of the present invention.
Figure 6:
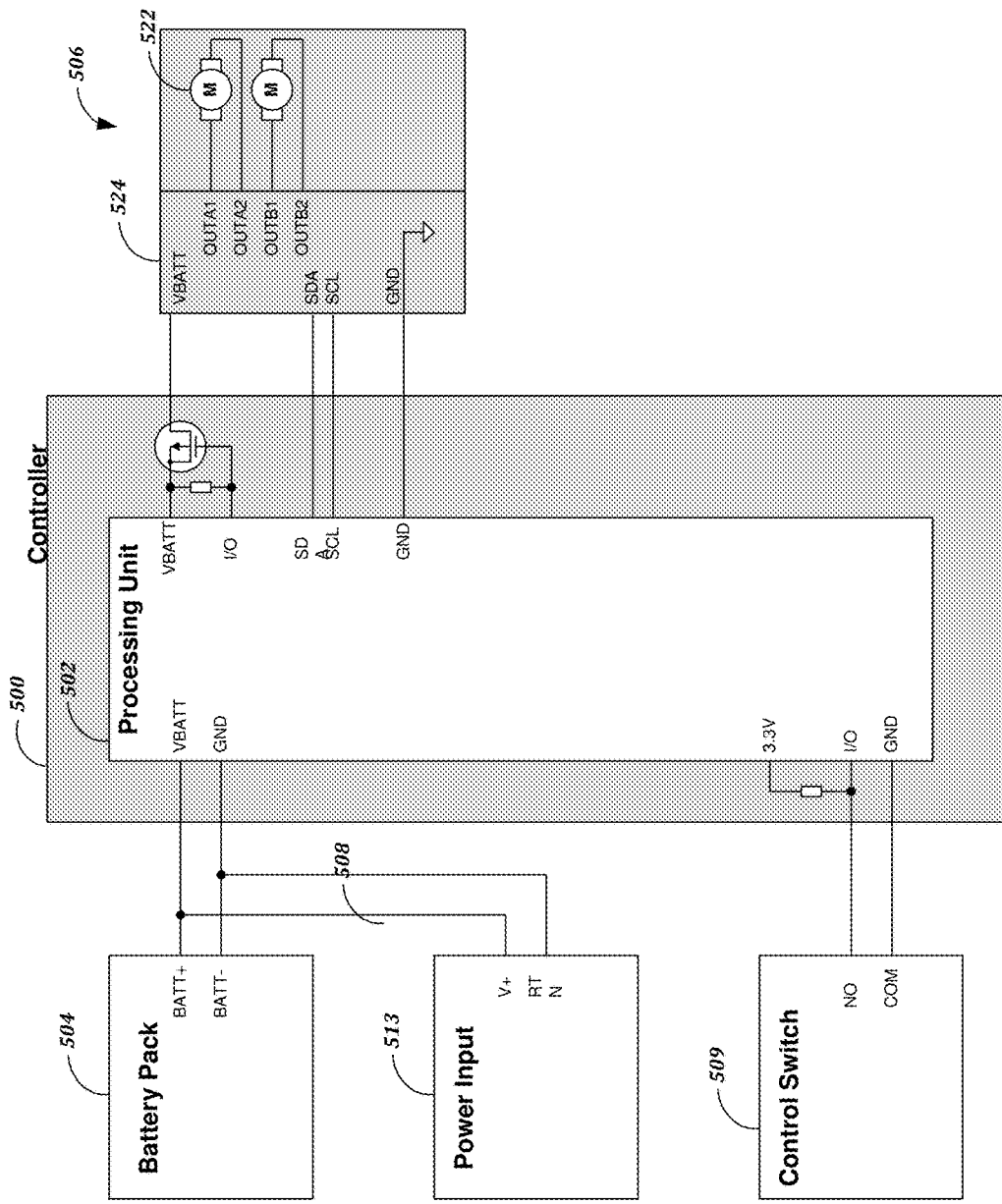
FIG. 6 show a diagram of a component configuration of the disclosed footwear in accordance with another exemplary embodiment of the present invention.
Figure 7:
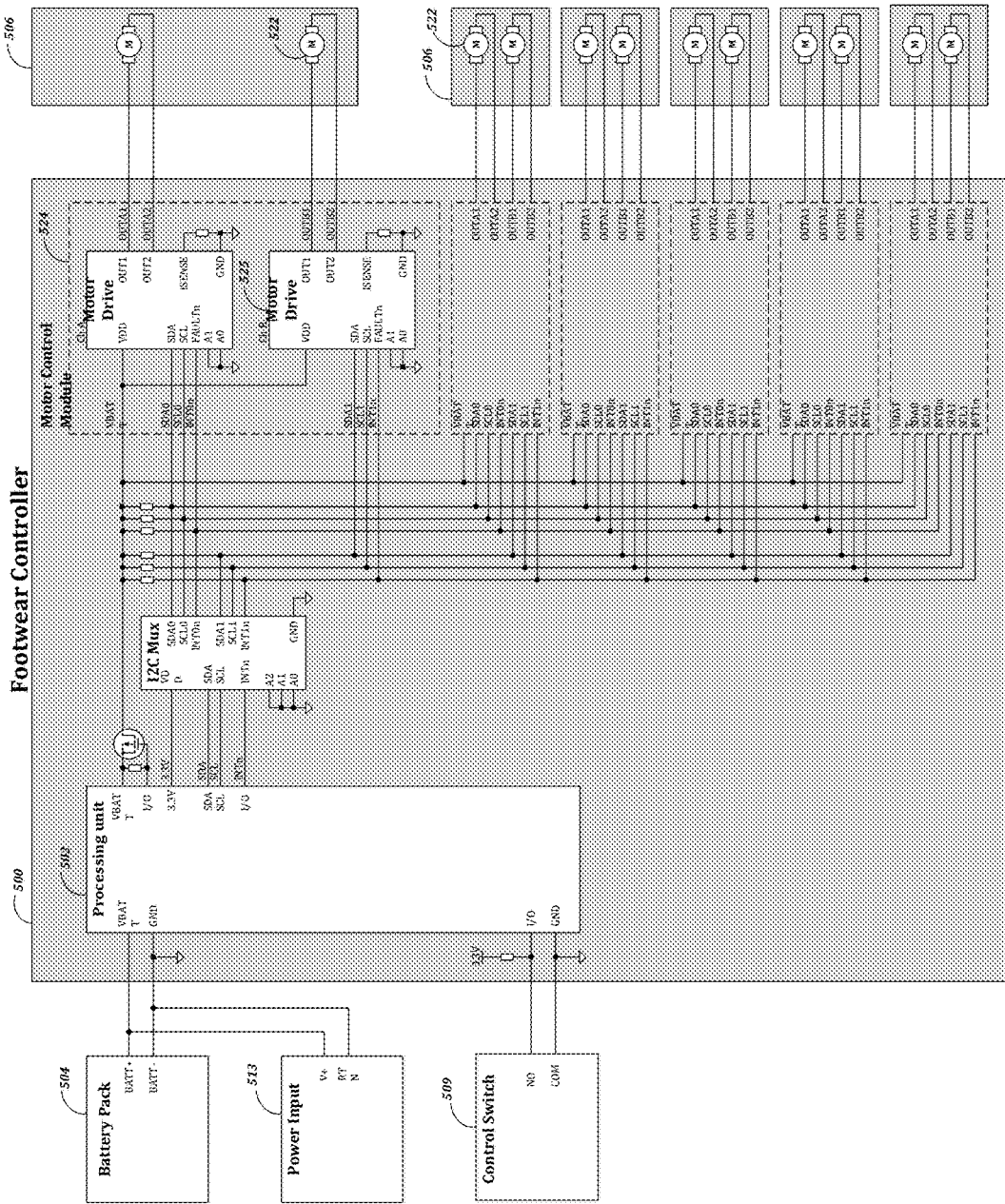
FIG. 7 show a diagram of a component configuration of the disclosed footwear in accordance with another exemplary embodiment of the present invention.

FIGS. 5-7 show diagrams of component configurations of the disclosed footwear in accordance with the present invention. FIG. 5 illustrates one example of an internal component configuration comprising a controller 500 containing a processing unit 502, battery back 504, voltage regulator 512, power switch 508 (e.g., MOSFET), battery management module 510 (e.g., fuel gauge), antenna 520 (e.g., Bluetooth LE antenna), and transceiver 522 (e.g., Bluetooth LE transceiver). In this embodiment, the system has wireless charging system comprising a battery charging module 514, wireless power receiver 518 (e.g., wireless power coil), and wireless power control module 516. In some embodiments, the controller 500 and above component are located in the same area of the article of footwear, for example, disposed within the sole. In this embodiment, the user can simply set the article of footwear on a compatible wireless charging mat or cradle to charge the battery in the article of footwear. In further aspects, the controller is in operable communication and configured to control one or more vibration device 506, located on a portion of the foot away from the sole. The vibration device 506 comprises a pair of vibrational elements 522, in some embodiments, may further optionally contain a vibrational motor control module 524.

In some embodiments, the internal components of the system may be configured in a distributed motor control configuration as shown in FIG. 6. In this configuration, the controller 500, along with a processing unit 502 (which may have an integrated communication module), battery back 504, power input 513, and control switch 509 may be located in one portion of the show in operable communication and configured to control multiple vibration devices 506 located in a remote part of the shoe. Here, the vibration device 506 contain a pair of vibrational elements 522 (e.g., vibration motors) and a vibrational motor control module 524 within vibration device casing.

In other embodiments, the internal components of the system may be configured in a centralized motor control configuration as shown in FIG. 7. Here, the vibrational motor control module 524 with a motor drive 525 for each channel is centrally located with the controller 500, and the remotely located vibration devices 506 only contain the vibrational elements 522 (e.g., vibration motors).

In further aspects, the upper can be comprised of fabric, cloth, plastic, woven or non-woven, natural or synthetic, leather, polyurethane (PU), microfiber leather, synthetic leather, and PU leather, nylon, cotton or the like. In some aspects, the upper can be comprised of a blend of synthetic and breathable cotton materials with appropriate cushioning materials for providing good comfort.

In further aspects, the sole can be comprised of any suitable material, such as, for example, rubber, high density cushioning foam, foam and fabric, or other material adapted for ground impact. In some aspects, the sole may comprise a tread pattern to provide traction. In other aspects, the sole may contain a flat bottom.

In various aspects, the components of the disclosed devices and footwear can be detachably attached. In further aspects, the components can be connected by a connecting means. In still further aspects, the connecting means can comprise a fitting, insert, adhesive, brazing, soldering, welding, spot weld, screw with nut, rivet, threading, friction fit, snap-fit, twist-lock, or interlocking mechanism or a combination thereof. In yet further aspects, the connection can be achieved using a snap, friction fitting, snap ring, O-ring, pressure fitting, clip, clasp, and the like. The snap ring or O-ring can be retained within a groove to accommodate the snap ring or O-ring. In a further aspect, the system can comprise an engagement means for coupling and holding components together. In a further aspect, the engagement means can be a screwing mechanism, a click-lock mechanism, or friction mechanism, or the like. In still further aspects, the components, for example, vibration devices, can be laminated to various portions of the footwear.

In a still further aspect, the device and system components can be integrally or mechanically attached to other components. In a yet further aspect, the disclosed components can be connected, attached, or mounted using a connecting means, the connecting means comprising a fitting, insert, adhesive, brazing, soldering, welding, spot weld, screw with nut, rivet, fitting, insert, threading, friction fit, or snap-fit or a combination thereof.

According to various aspects of the disclosure, the footwear and systems of the present invention provides a number of advantages of current options. The combination of inventive vibration configurations, vibration device construction and positioning allow the disclosed footwear and systems to be more effective in reducing pain and discomfort experienced by a user, such as for example, in a user's foot. Without wishing to be bound by any particular theory, it is believed that the vibrational effects provided by the footwear and systems of the present invention may block nerve transmissions from sensory nerves so that the pain and/or pain sensations from the foot to the brain and/or spinal cord are blocked. In further aspects, the disclosed footwear and systems can be used to relieve pain in the foot and/or stress throughout the entire body. In still further aspects, the disclosed footwear and systems can be used relieve body pain and mental pain or stress. In some aspects, the vibrational effects delivered may provide a local effect to a foot surface and underlying tissue within 50 cm from the site of application. In other aspects, application of vibration may have a more systemic effect by triggering a response in the local area of the foot, such as a nerve, that may have effects at a remote site location, such as triggering a nerve response at the site of application that blocks nerve transmission of pain or sensation to other areas.

In further aspects, the disclosed footwear with one or more vibration devices can selectively operable to relieve pain in the foot and ankle region. In still further aspects, application software (an app) on a wireless device such as a mobile phone may be used to activate and de-activate and/or otherwise control the vibrations emitted by the one or more vibration devices in the article of footwear. In yet further aspects, the disclosed footwear may be equipped with wireless technology to communicate with the app on the wireless device. In even further aspects, the app may provide at least ones of: a graphic image of the user's foot to indicate where (and/or other characteristics of the vibrations) the vibration device(s) are delivering vibrations to the user's foot at the time of operation, possible areas of the user's foot to indicate where (and/or other characteristics of the vibrations) the vibration device(s) may be made to deliver vibrations, telemetry data received from the sensors in the footwear. In still further aspects, the disclosed footwear may be made with an inflatable air pocket on its top. In yet further aspects, the disclosed footwear may be made to include compression technology for a good fit on the foot of a user. In even further aspects, the article of footwear may be made to include durable outer sole and comfortable inner sole.

Figure 8:
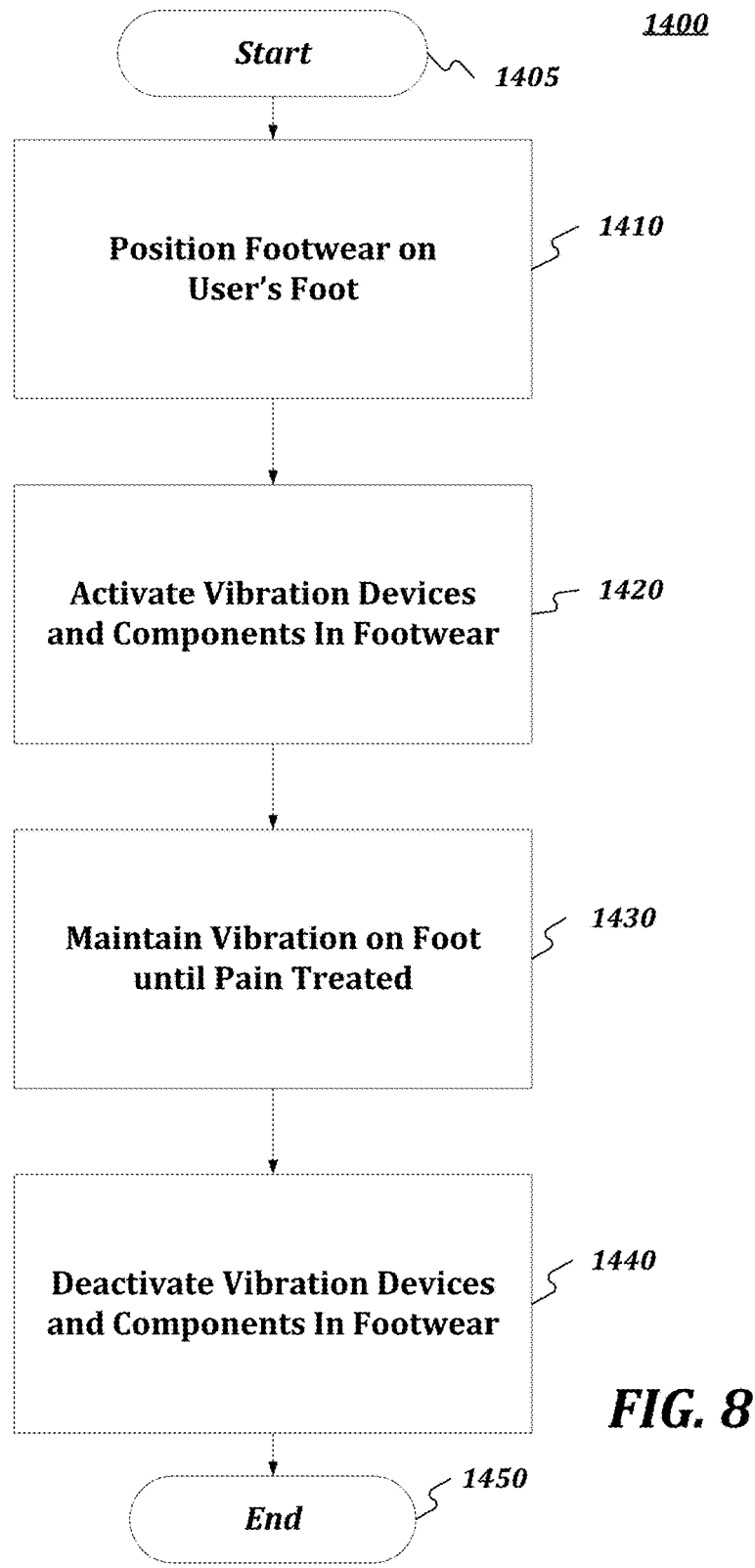
FIG. 8 shows a method for using the disclosed footwear and systems in accordance with another exemplary embodiment of the present invention.

Also disclosed herein are methods of using the disclosed footwear and systems. For example, in another exemplary aspect, the present disclosure provides a method for reducing pain or discomfort using a disclosed article of footwear or system. In further aspects, the pain or discomfort may by located in the foot. In still further aspects, the pain or discomfort is not limited to pain or discomfort located in the foot, and may be pain in other parts of the body, such as, for example, mental pain or stress or body pain. FIG. 8 is a flow chart setting forth the general stages involved in a method 1400 consistent with an embodiment of the disclosure for operating the disclosed footwear and systems. Method 1400 may be implemented using, at least in part, a controller 1500 (e.g., on-board computing device) as described in more detail below with respect to FIG. 9. Controller 1500 may comprise a controller for operating the vibration devices and footwear components as well as well as performing other operational tasks, including, but not limited to, vibrational control and parameters, and communication. As such, controller 1500 may be in operative configuration and communication with, for example, but not be limited to, vibrational elements, thermal elements, activating switch, communication module, power source, power regulator, various telemetry sensors, transceivers and antennas. As will be detailed with reference to FIG. 9, controller 1500 may comprise a remote communication module to enable remotely operation as described herein. In other embodiments, controller 1500 may be completely self-operating upon configuration.

Furthermore, although stages are disclosed with reference to controller 1500, it should be understood that a plurality of other components may enable the operation of method 1400, including, but not limited to, other computing components, mechanical components, environment properties (e.g., temperature), user conditions, and the like.

Further still, although the stages illustrated by the flow charts are disclosed in a particular order, it should be understood that the order is disclosed for illustrative purposes only. Stages may be combined, separated, reordered, and various intermediary stages may exist. Accordingly, it should be understood that the various stages illustrated within the flow chart may be, in various embodiments, performed in arrangements that differ from the ones illustrated. Moreover, various stages may be added or removed from the flow charts without altering or deterring from the fundamental scope of the depicted methods and systems disclosed herein.

Method 1400 may begin at starting block 1405 and proceed to stage 1410, where the footwear may be placed on a foot of a user. From stage 1410, where the footwear is positioned on the user's foot, method 1400 may proceed to stage 1420 where the vibration devices and/or components may be activated. The activation of footwear components, though disclosed in a particular order for illustrative purposes, may occur in other arrangements. Upon activation, one or more of vibrational devices and/or vibrational elements may begin to vibrate. In some embodiments where present, one or more thermal elements may be activated to provide heat and/or cool to the user's foot.

In various aspects, an advantage of the invention can be that it allows a user to activate the vibration devices in an article of footwear remotely from the article of footwear. In further aspects, a user does not have to pick up the article of footwear to: activate its operation, to shut off operation, and/or in embodiments that allow for adjustment, to adjust the vibration level. In still further aspects, a user may activate or de-activate (and/or otherwise control operation of) the vibration devices by using a control unit, such as a wireless device or mobile device that is in operative communication with the vibration devices of the article of footwear. The wireless device may be a device that may be used for additional purposes other than use with the invention such as a mobile phone, tablet computer, notebook computer, desktop computer, etc. In an embodiment, the invention may provide a specialized wireless device for use with the invention. The specialized wireless device may include other uses, if its use is not limited to this particular embodiment of the invention.

As provided in more detail herein, the control unit used to control the vibration devices of the article of footwear may include an application or application software (an "app") specifically created for such usage. Advantageously, the user may download and/or otherwise obtain the app from sources that supply apps such as independent developers and app stores. The app as used with embodiments of the invention communicates wirelessly, such as by using Bluetooth or the like technology.

Controller 1500 (e.g., on-board computing-device) may automatically activate vibrational elements instantly or after a set amount of time has passed since the launch. In other embodiments, activation may occur upon certain reading from on-board sensors (e.g., including, but not limited to, sensors deployed in the footwear). For example, activation of one or more vibrational elements may be dependent on certain environmental factors and/or user conditions such as, for example, temperature, blood pressure, acceleration, and the like. Controller 1500 may be configured to trigger activation of various footwear and device components upon the satisfaction of certain pre-set conditions. Such conditions may be defined prior to activation.

From stage 1420, where the footwear and device components are activated, method 1400 may proceed to stage 1430, where the vibration and/or thermal effects may be maintaining the site of the foot for a time sufficient to reduce pain or discomfort at the site and/or stress in the body. From stage 1430, where the footwear is used to perform a treatment, method 1400 may proceed to stage 1440, where the footwear and device components are turned off. After stage 1440, method 1400 may end at stage 1450.

In further aspects, another method of the present invention can comprise reducing the pain or discomfort, such as those caused by arthritis or muscle disorders, the method comprising contacting a vibration device in footwear of the present invention between the spinal cord and the site in the foot where the pain or discomfort is initiated; activating vibration by the vibration device in an intermittent or continuous vibration, optionally applying thermal effect simultaneously with the vibration, vibrating for a sufficient time to interfere with nerve transmission or transmission of pain signals. In still further aspects, another method of the present invention can comprise reducing mental stress in a user, the method comprising contacting a vibration device in footwear of the present invention to a site in the user's foot, initiating vibration by the vibration device in the footwear, and reducing the sensation of stress, for example, by interfering with the transmission of nerve signals and/or relaxing muscles in the user's foot.

In further aspects, another method of the present invention can comprise treating neuropathic pain from nerve pain such as phantom pain or the like. A method of interfering with transmission of neuropathic pain signals may comprise a) contacting a vibration device in footwear of the present invention with an area on the foot surface of a user between the spinal cord and the site of nerve pain, so that at least a portion of the application area of the vibration device contacts a portion of the foot surface of the user; b) initiating vibration by the vibration device in the footwear in an intermittent or continuous vibration, and optionally applying a thermal effect simultaneously with the vibration, and c) continuing the vibration effect at the foot of for a time sufficient to reduce the pain felt from the site. The thermal effect may cold or warm.

In various aspects, methods of the present invention comprise providing a vibration device in the footwear of the present invention externally to the skin surface of a user's foot. In some aspects, the vibration device in the footwear of the present invention may be placed at a site on the foot experiencing pain, itching, burning, or may be placed proximal to such sites. In other aspects, the pain is related to mental stress or generalized or diffuse body pain. In further aspects, one vibratory device in the footwear is activated at one site for a period of time while one or more other vibratory devices in the footwear are simultaneously or sequentially activated at other sites in the foot. In still further aspects, methods of the present invention allow for increased blood flow, relaxation of muscles, relaxation of overactive nerves, reduction of pain, reduction of stress or unpleasant sensations, increased healing, and overall increased well-being and function of the user when compared to the user's state prior to use of the footwear of the present invention.

In some aspects, the vibrational effects delivered may provide a local effect to a foot surface and underlying tissue within 50 cm or less from the site of application. In other aspects, application of vibration may have a more systemic effect by triggering a response in the local area of the foot, such as a nerve or muscle, that may have effects at a remote location, such as triggering a nerve response at the site of application that blocks nerve transmission of pain or sensation to other areas or relaxing muscles that are causing stress to other parts of the body.

In further aspects, the vibration can help to reduce pain by surmounting the pain nerves. In still further aspects, the footwear and systems can help reduce pain, and in turn help relax tense muscles. Without wishing to be bound by any particular theory, it is believed that the vibrational effects provided by the footwear and systems of the present invention may block nerve transmissions from sensory nerves so that the pain and/or pain sensations from the foot to the brain and/or spinal cord are blocked.

In further aspects, the vibration device in the footwear may be allowed to act upon the user for a time necessary to initiate vibration effects which can be for a period of seconds up to a period of several minutes or more, or may be from greater than 0 seconds to about 120 minutes. If prolonged vibratory treatment is desired the footwear may be worn for a longer period to provide pain relief or relief from discomfort. Once the desired outcome is reached, the vibration devices in the footwear may be turned off and/or the footwear may be removed from the user. However, it is possible to leave the vibration devices in the footwear active and in contact with the user for prolonged periods of time. For example, the footwear may be left in place, and the vibration devices are then activated on an on-going schedule of time periods of use of the device and inactivity.

During all stages of the various methods, the footwear may be in operable communication with the user via antenna or wireless communication component. The user may receive various readings from the various footwear and device components. In some embodiments, the user may control the operation of the vibration devices and footwear during use. For example, the user may be able to control the vibration device and footwear components, including, but not limited to, vibrational elements, thermal elements, activating switch, communication module, power source, power regulator, various telemetry sensors, transceivers and antennas.

In other embodiments, integrated controller 1500 may be pre-configured with operational control instructions and/or data. In further aspects, embodiments of the footwear may be used for treating a plurality of pain and unpleasant sensations including, but not limited to, burning, itching, and throbbing.

In various aspects, the disclosed footwear and systems may comprise, but not be limited to, an integrated controller and/or on-board computing module. The computing module may be in operative configuration and communication with, for example, but not be limited to, vibrational elements, thermal elements, activating switch, communication module, power source, power regulator, various telemetry sensors, transceivers and antennas. Further, the computing module may be in operative communication with another computing device consistent with the description herein, and may comprise, but not be limited to, a wireless device, smart phone, desktop computer, laptop, a tablet, or mobile telecommunications device. Such remote devices may be used to control and/or configure integrated computing module (e.g., activation conditions, vibrational operating parameters and settings, and the like).

Moreover, the footwear may be in operative communication with a centralized server, such as, for example, a cloud computing service. Although operation has been described to be performed, in part, by a controller 1500, it should be understood that, in some embodiments, different operations may be performed by different networked elements in operative communication with controller 1500.

Embodiments of the present disclosure may comprise a system having a memory storage and a processing unit. The processing unit may be coupled to the memory storage, wherein the processing unit is configured to perform the stages of method 1400.

Figure 9:
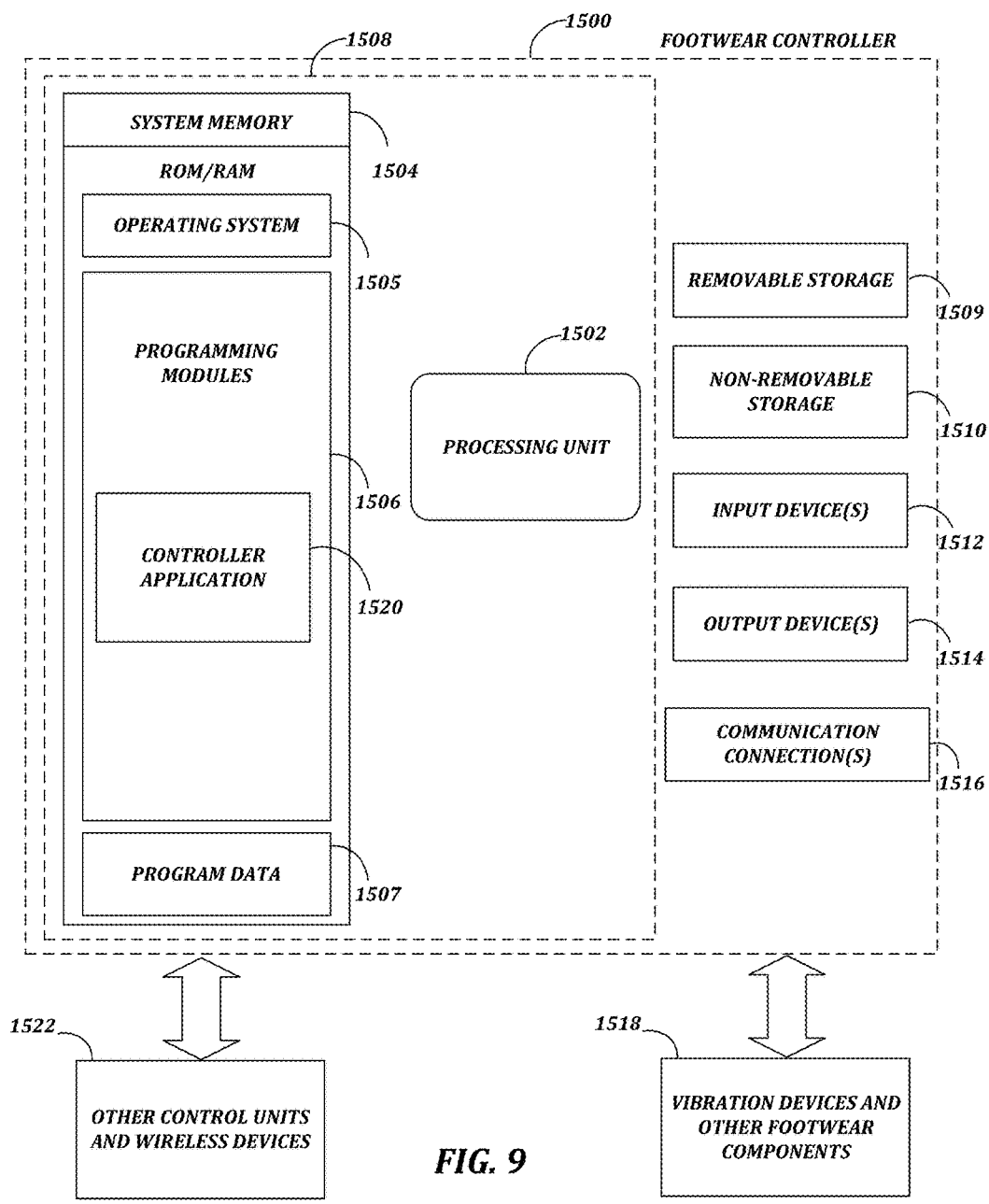
FIG. 9 shows a diagram of a system including a computing device for enabling operation of the disclosed footwear in accordance with another exemplary embodiment of the present invention.

FIG. 9 is a block diagram of a system including controller 1500. Consistent with an embodiment of the disclosure, the aforementioned memory storage and processing unit may be implemented in a computing device, such as controller 1500. Any suitable combination of hardware, software, or firmware may be used to implement the memory storage and processing unit. For example, the memory storage and processing unit may be implemented with controller 1500 or any of vibration devices and footwear components 1518, or any other control unit and wireless devices 1522, in combination with controller 1500. Other vibration devices and components 1518 may comprise, for example, but not be limited to, control mechanisms, vibrational elements, thermal elements, activating switch, communication module, power source, power regulator, various telemetry sensors, transceivers and antennas. The aforementioned system, device, and processors are examples and other systems, devices, and processors may comprise the aforementioned memory storage and processing unit, consistent with embodiments of the disclosure.

With reference to FIG. 8, a system consistent with an embodiment of the disclosure may include a computing device, such as controller 1500. In a basic configuration, controller 1500 may include at least one processing unit 1502 and a system memory 1504. Depending on the configuration and type of computing device, system memory 1504 may comprise, but is not limited to, volatile (e.g. random access memory (RAM)), non-volatile (e.g. read-only memory (ROM)), flash memory, or any combination. System memory 1504 may include operating system 1505, one or more programming modules 1506, and may include a program data 1507. Operating system 1505, for example, may be suitable for controlling controller 1500's operation. In one embodiment, programming modules 1506 may include controller application ("app") 1520. Furthermore, embodiments of the disclosure may be practiced in conjunction with a graphics library, other operating systems, or any other application program and is not limited to any particular application or system. This basic configuration is illustrated in FIG. 9 by those components within a dashed line 1508.

Advantageously, the app may provide a user with information as well as be the user's interface to operating the embodiment of the invention. The app may include one or more graphic user interfaces (GUIs). Among the GUIs of the app may be a GUI allowing the user to pick which, if there is more than one, vibration device and/or element to activate, and to select (if available) one or more operating parameters or characteristics (such as amplitude or frequency) of the vibration of the vibration device(s). The user may be able to adjust such selections without having to deactivate the embodiment from a GUI of the app. The user may also use the app to turn on and turn off the device components.

Another advantage of the app is that the app may present the user with a GUI that depicts the user's foot (or a generic foot) and shows where the vibrations are being applied. The GUI may include additional or other information relating to the vibrations being applied such as the strength (amplitude) or frequency (speed) of the vibrations. The additional or other information may be color coded and/or otherwise presented so as to be readily understood by the user by looking at the GUI of the app. The app may also present the user with information received from the device components, such as environmental and telemetry data.

Controller 1500 may have additional features or functionality. For example, controller 1500 may also include additional data storage devices (removable and/or non-removable) such as, for example, magnetic disks, optical disks, or tape. Such additional storage is illustrated in FIG. 9 by a removable storage 1509 and a non-removable storage 1510. Computer storage media may include volatile and nonvolatile, removable and non-removable media implemented in any method or technology for storage of information, such as computer readable instructions, data structures, program modules, or other data. System memory 1504, removable storage 1509, and non-removable storage 1510 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by controller 1500. Any such computer storage media may be part of device 1500. Controller 1500 may also be operative with input device(s) 1512 such as a keyboard, a mouse, a pen, a sound input device, a touch input device, etc. Input device(s) 1512 may be used to, for example, manually access and program controller 1500. Output device(s) 1514 such as a display, speakers, a printer, etc. may also be included. The aforementioned devices are examples and others may be used.

Controller 1500 may also contain a communication connection 1516 that may allow device 1500 to communicate with other control units and wireless devices 1522 as well as vibration devices and other footwear components 1518 (e.g., transceivers, sensors, thermal elements), such as over an encrypted network in a distributed computing environment. Communication connection 1516 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, Bluetooth, radio frequency (RF), infrared, and other wireless media. The term computer readable media as used herein may include both storage media and communication media.

As stated above, a number of program modules and data files may be stored in system memory 1504, including operating system 1505. While executing on processing unit 1502, programming modules 1506 (e.g., footwear controller application 1520) may perform processes including, for example, one or more of stages or portions of stages of method 1400 as described above. App 1520 may be configured to operate footwear and device components 1518 and receive instructions from, for example, communications connections module 1516. The aforementioned process is an example, and processing unit 1502 may perform other processes.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, multiprocessor systems, microprocessor-based or programmable consumer electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way appreciably intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein can be different from the actual publication dates, which can require independent confirmation.

The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A system for reducing pain, the system comprising:
an article of footwear comprising an upper connected to a sole;
at least one vibration device disposed within the upper, the at least one vibration device comprising: a casing comprising an application area, and at least one vibrational element contained within the casing, the at least one vibrational element configured to deliver vibrations directly to a surface on a top portion of a foot of a user of the footwear; wherein the casing comprises interior walls defining interior sections sized and shaped to contain the at least one vibrational element; wherein substantially all of the vibrational energy emitted from the at least one vibrational element is transmitted through the application area of the casing directly to the user's foot; and wherein the at least one vibration device is not disposed within or positioned on the sole;
a controller communicatively connected to the at least one vibration device and configured to control operation of the at least one vibration device based on instructions regarding operation of the at least one vibration device; and
a control unit communicatively connected to the controller and configured to transmit instructions regarding the operation of the at least one vibration device to the controller;
wherein the casing is manufactured from a pliant material comprising at least one of: natural or synthetic woven or non-woven fabrics, rubbers, polymer materials, and silicone-based materials; and wherein there is an absence of open space between the interior casing walls and the at least one vibrational element.

2. The system of claim 1, wherein the control unit comprises a switch in operative communication with the at least one vibration device for selectively activating the at least one vibration device.

3. The system of claim 1, wherein the control unit comprises a wireless device having application software configured to transmit instructions regarding the operation of the at least one vibration device to the controller.

4. The system of claim 3, wherein the application software is operational to present information regarding the operation of the at least one vibration device to the user via one or more graphic user interfaces on the wireless device.

5. The system of claim 3, wherein the at least one vibration device comprises a plurality of vibrational elements within the casing.

6. The system of claim 5, wherein the at least one vibration device further comprises at least one thermal element capable of being heated or cooled.

7. The system of claim 5, wherein the vibrations of the at least one vibration element comprise multiple vibration cycles.

8. The system of claim 5, wherein a vibration per minute of the plurality of vibrational elements cycle between from about 100 to about 15,000 vibrations per minute.

9. The system of claim 5, wherein each of the plurality of vibrational elements contained within the casing vibrates at different vibrations per minute.

10. The system of claim 9, wherein the system comprises a plurality of vibration devices disposed within a plurality of positions on the upper corresponding to a plurality of locations on the top portion of the foot selected from an ankle location and a top location of the foot, each of the plurality of vibration devices comprising a plurality of vibrational elements and a casing comprises interior walls defining interior sections sized and shaped to contain the plurality of vibrational elements.

11. The system of claim 10, wherein each of the plurality of vibration devices is not disposed within or positioned on the sole.

12. The system of claim 10, wherein each of the plurality of vibration devices does not comprise any open space between the interior casing walls and the plurality of vibrational elements.

13. The system of claim 1, wherein the casing is shaped to conform to a contour of a surface of the foot.

14. The system of claim 1, wherein the article of footwear comprises a shoe.

15. A method for reducing pain or discomfort in a user; the method comprising:
providing an article of footwear having a plurality of vibration devices capable of delivering vibrations to the user's foot;
operatively positioning the article of footwear on the user's foot such that the plurality of vibration devices provide vibration directly to at least one site on at least one of an ankle and top portion of the user's foot;
activating the plurality of vibration devices using a control device in operative communication with the plurality of vibration devices for selectively activating the plurality of vibration devices; and
maintaining the plurality of vibration devices at the at least one site of the foot for a time sufficient to reduce the pain or discomfort; and
wherein each of the plurality of vibration devices is not located on or in direct physical contact with a sole of the user's foot;
wherein the plurality of vibration devices each comprise a casing comprising an application area, and at least one vibrational element contained within the casing, the at least one vibrational element configured to deliver vibrations directly to a surface on a top portion of a foot of a user of the footwear; wherein the casing comprises interior walls defining interior sections sized and shaped to contain the at least one vibrational element and wherein there is an absence of open space between the interior casing walls and the at least one vibrational element.

16. The method of claim 15, wherein the control device comprises a wireless device having application software configured to transmit instructions regarding an operation of the plurality of vibration devices.

17. The method of claim 15, wherein each vibration device comprises a plurality of vibrational elements;
wherein the casing of each vibration device comprises interior walls defining interior sections sized and shaped to contain the plurality of vibrational elements; and wherein the casing of each vibration device is free of open space between the interior casing walls and the plurality of vibrational elements such that substantially all of the vibrational energy emitted from the plurality of vibrational elements is transmitted through the casing of each vibration device to the at least one site on the user's foot.

18. The method of claim 17, wherein the pain or discomfort is at least one of: body pain and mental stress.

* * * * *